United States Patent
Rhinehart et al.

[11] Patent Number: 5,947,935
[45] Date of Patent: Sep. 7, 1999

[54] SYRINGES, SYRINGE PLUNGERS AND INJECTOR SYSTEMS

[75] Inventors: Edward J. Rhinehart, Monroeville; David M. Reilly, Glenshaw; Mark W. Hitchins, Sewickley; Anthony S. McCoppin, Butler, all of Pa.

[73] Assignee: Medrad, Inc., Indianola, Pa.

[21] Appl. No.: 08/978,226

[22] Filed: Nov. 25, 1997

Related U.S. Application Data

[63] Continuation-in-part of application No. 08/748,258, Nov. 12, 1996, Pat. No. 5,873,861.

[51] Int. Cl.⁶ .................................................. A61M 25/00
[52] U.S. Cl. ........................... 604/218; 604/131; 604/151
[58] Field of Search ................................. 604/218, 131, 604/152, 220, 221, 232, 151

[56] References Cited

U.S. PATENT DOCUMENTS

| | | |
|---|---|---|
| 3,705,582 | 12/1972 | Stumpf . |
| 3,902,491 | 9/1975 | Lajus . |
| 4,006,736 | 2/1977 | Kranys . |
| 4,180,006 | 12/1979 | Walters . |
| 4,628,969 | 12/1986 | Jurgens, Jr. . |
| 4,636,198 | 1/1987 | Stade . |
| 4,677,980 | 7/1987 | Reilly . |
| 4,705,509 | 11/1987 | Stade . |
| 4,718,463 | 1/1988 | Jurgens, Jr. . |
| 4,863,427 | 9/1989 | Cocchi . |
| 4,869,720 | 9/1989 | Chernack . |
| 4,911,695 | 3/1990 | Lindner . |
| 5,062,832 | 11/1991 | Seghi . |
| 5,256,154 | 10/1993 | Liebert . |
| 5,300,031 | 4/1994 | Neer . |
| 5,314,415 | 5/1994 | Liebert . |
| 5,373,684 | 12/1994 | Vacca . |
| 5,383,858 | 1/1995 | Reilly . |
| 5,520,653 | 5/1996 | Reilly et al. . |
| 5,531,710 | 7/1996 | Dang . |
| 5,535,746 | 7/1996 | Hoover et al. . |

FOREIGN PATENT DOCUMENTS

| | | |
|---|---|---|
| 0 111 724 A2 | 6/1984 | European Pat. Off. . |
| 0 482 677 A1 | 4/1992 | European Pat. Off. . |

OTHER PUBLICATIONS

International Search Report for Counterpart International Application No. PCT/US 97/20122.
Mallinckrodt New Ultraject Prefilled Syringe Brochure for 30ml and 50ml syringes.
Drawing of Dual Flange Injector Head (publicly disclosed in Jul. of 1995).

*Primary Examiner*—John D. Yasko
*Attorney, Agent, or Firm*—Gregory L. Bradley

[57] ABSTRACT

The present invention provides a connection mechanism adapted to make a releasable connection between a syringe plunger and a drive member of an injector. The drive member is preferably movable in a generally reciprocal linear manner to control movement of the plunger within the syringe. The connection mechanism comprises at least one capture member attached to the plunger. The capture member forms a releasable connection with the drive member upon contact of the drive member during linear forward motion of the drive member when the capture member is rotated relative to the drive member to an engagement position. The capture member is further adapted to disconnect from the drive member upon rotation of the capture member relative to the drive member to a disengagement position.

41 Claims, 13 Drawing Sheets

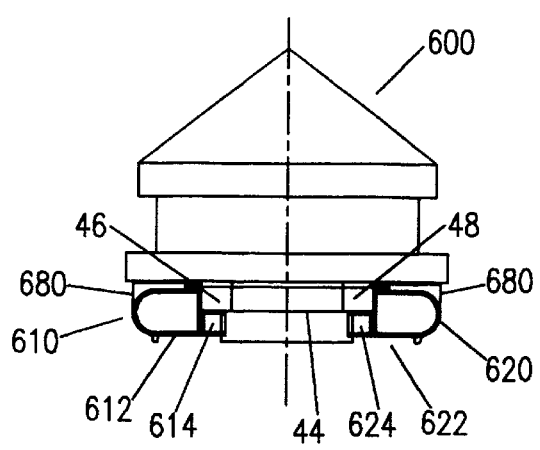
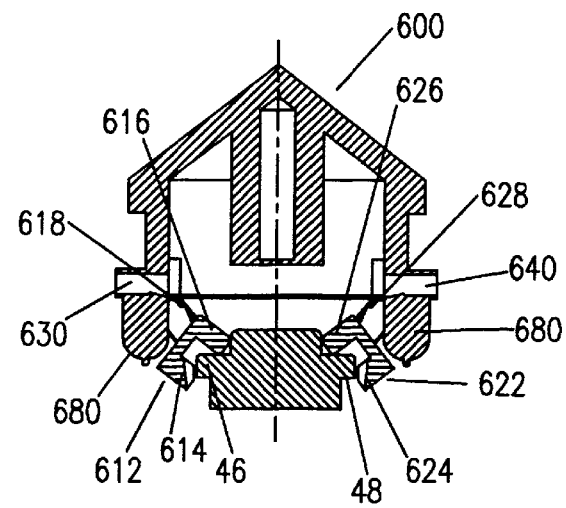
FIGURE 7A
FIGURE 7B
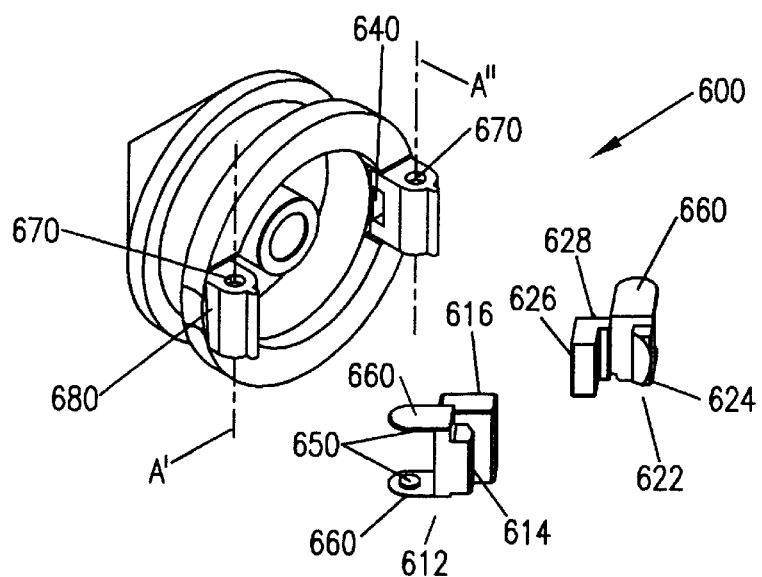
FIGURE 7D

SYRINGES, SYRINGE PLUNGERS AND INJECTOR SYSTEMS

CROSS-REFERENCE TO RELATED APPLICATION

The present application is a continuation-in-part of application Ser. No. 08/748,258, filed on Nov. 12, 1996, now U.S. Pat. No. 5,873,861 the contents of which are hereby incorporated by reference.

FIELD OF THE INVENTION

The present invention relates to syringes, syringe plungers and injector systems and, more particularly, to syringes, syringe plungers and injector systems having a releasable mechanism operable to engage a drive member of a powered injector.

BACKGROUND OF THE INVENTION

A number of injector-actuated syringes and powered injectors for use in medical procedures such as angiography, computer tomography and NMR/MRI have been developed. U.S. Pat. No. 4,006,736, for example, discloses an injector and syringe for injecting fluid into the vascular system of a human being or an animal.

Typically, such injectors comprise drive members, such as pistons, that connect to a syringe plunger. For example, U.S. Pat. No. 4,677,980, the contents of which are hereby incorporated by reference, discloses an angiographic injector and syringe wherein the drive member of the injector can be connected to, or disconnected from, the syringe plunger at any point along the travel path of the plunger within the syringe by means of a releasable mechanism.

Although substantial advances have been made in the design of injectors and syringe plungers for use therewith, it remains desirable to develop improved designs of injectors and syringes to facilitate injection procedures and to provide suitable interface connections between injector drive members and syringe plungers.

SUMMARY OF THE INVENTION

In a preferred aspect, the present invention provides a mechanism adapted to form a releasable connection between a syringe plunger and a drive member of an injector. The drive member is preferably movable in a generally reciprocal linear manner to control the movement of the plunger within the syringe. In a preferred embodiment, the connection mechanism comprises at least two capture members attached to the plunger. In an alternate preferred embodiment, however, the capture members instead may be attached to the drive member.

In a preferred embodiment, the capture members on the plunger form a releasable connection with the drive member upon contact therewith. During linear forward motion, the drive member contacts and is captured by the capture members. As a result, the forward and rearward movements of the drive member and the plunger within the syringe are coordinated. Thus, while the drive member and the capture members are connected in the engagement position, the reciprocal linear motion of the drive member controls the position of the plunger within the syringe.

In a preferred embodiment, to release the plunger from the drive member the capture members are first rotated relative to the drive member to a disengagement position. The drive member is then retracted relative to the capture members to disengage the drive member from the plunger. After the drive member and the plunger are disconnected, the syringe may be removed from the injector.

In other preferred aspects, the present invention provides syringes, syringe plungers, injectors and injector systems incorporating the release mechanisms described herein.

The release mechanisms of the present invention provide readily releasable connections between syringe plungers and drive pistons of injectors. With currently-available syringe plungers for injector systems, the drive member and plunger are generally required to be accurately positioned both longitudinally and radially with respect to each other before a connection can be formed therebetween. By utilizing the releasable mechanisms of the present invention, however, users of injector systems need only ensure that the plunger and the drive member are rotated relative to each other to an engagement position to complete a connection therebetween. When the plunger and the drive member are rotated to the engagement position, the capture members of the plunger engage and capture the drive member upon forward movement of the drive member, regardless of the longitudinal position of the plunger.

BRIEF DESCRIPTION OF THE DRAWINGS

Other aspects of the invention and their advantages will be discerned from the following detailed description when read in connection with the accompanying drawings, in which:

FIG. 7A illustrates a side view of another embodiment of a plunger assembly in which the capture members are moveably hinged to capture and retain a piston, which is shown to be retained by the capture members.

FIG. 7B illustrates a side, cross-sectional view of the plunger assembly of FIG. 7A in which the piston is shown in its initial contact position with the capture members.

FIG. 7D illustrates a bottom perspective view of the plunger assembly of FIG. 7A in which the movable portions of the capture members are disconnected.

DETAILED DESCRIPTION OF THE INVENTION

The present invention provides, in a preferred aspect, releasable connection mechanisms operable to releasably connect syringe plungers with injector drive members. The releasable mechanisms described herein may be incorporated in, inter alia, syringes, syringe plungers, injectors and injector systems to facilitate injector system use.

Figure 1:
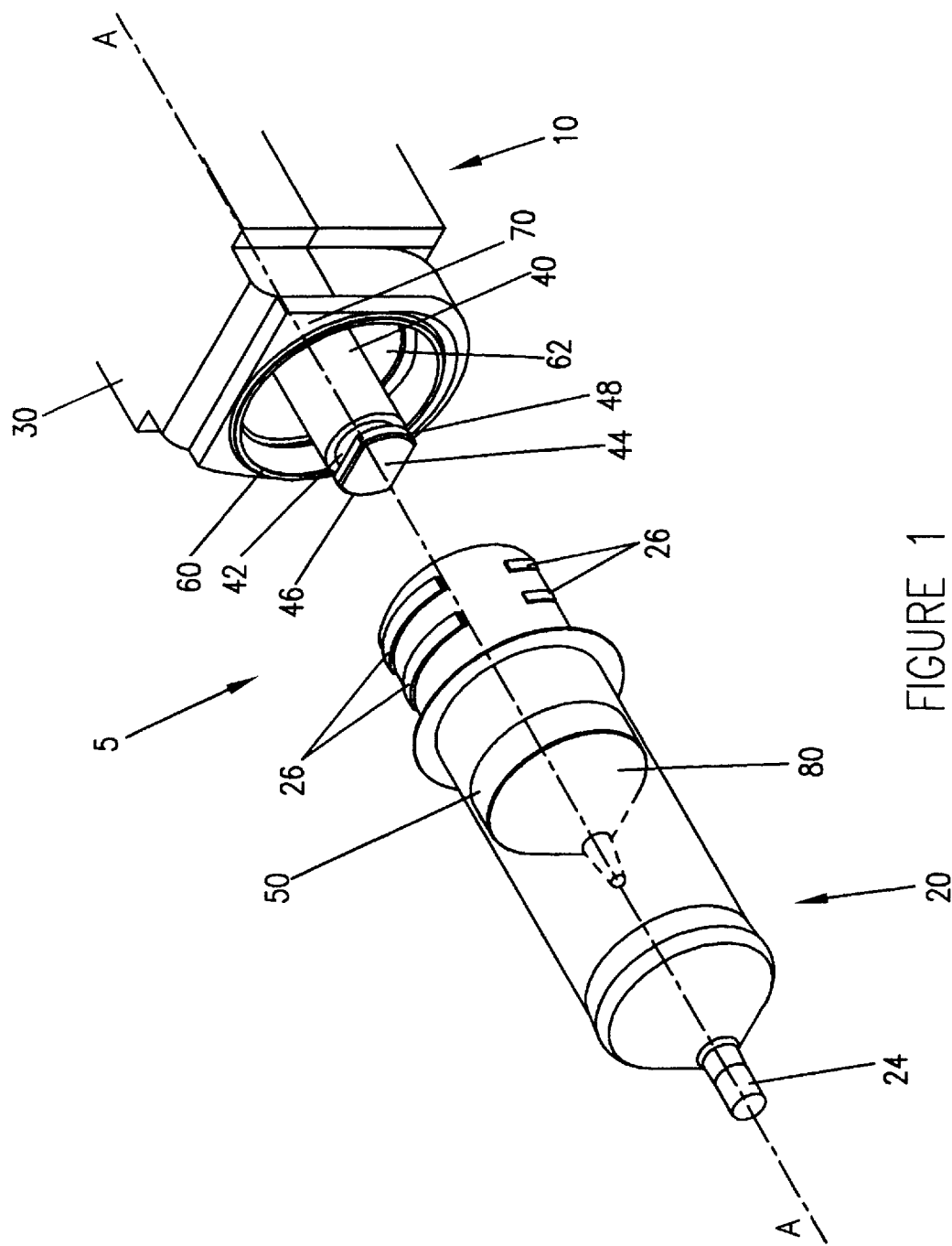
FIG. 1 illustrates an embodiment of an injector system.

Turning now to the drawings, an embodiment of a front-loading injector system 5 is illustrated in FIG. 1. Injector system 5 includes an injector 10 and a syringe 20. Injector housing 30 of injector 10 preferably includes a reciprocating drive member or piston 40 therein which cooperates with a syringe plunger 50 to inject an injection fluid or liquid medium from the interior of syringe 20 into a patient. Piston 40 is extendible and retractable via a powered means preferably contained within injector housing 30 and comprising, for example, a motor or hydraulic system, including appropriate gearing (not shown). As known in the art, injector housing 30 also preferably includes a motor controller for controlling operation of a motor and thereby controlling operation of piston 40.

As used herein to describe injection system 5, the terms "axial" or "axially" refer generally to an axis A around which system 5 (including, for example, piston 40, syringe 20 and plunger 50) are preferably formed (although not necessarily symmetrically therearound). The terms "proximal" or "rearward" refer generally to an axial direction toward the end of injector housing 30 opposite the end to which syringe 20 is mounted. The terms "distal" or "forward" refer generally to an axial direction toward a syringe tip 24 of syringe 20. The term "radial" refers generally to a direction normal to axis A.

Referring to FIG. 1, piston 40 moves axially forwardly and rearwardly through a retainer 60 comprising an opening 62 formed in a front wall 70 of injector housing 30. Opening 62 and syringe 20 preferably comprise cooperating means for securely affixing syringe 20 to front wall 70. Preferably, such securing means comprise a cooperating mounting mechanism formed upon the rearward portion of syringe 20 and a cooperating retainer 60 formed upon injector front wall 70. In a preferred embodiment, the mounting mechanism comprises retaining flanges which cooperate in a rotating manner with mounting flanges 26 positioned on the rear of syringe 20. Various such embodiments are disclosed in U.S. Pat. Nos. 4,677,980 and 5,388,858, as well as U.S. patent application Ser. No. 08/748,258, the contents of which are hereby incorporated by reference.

As illustrated in FIG. 1, plunger 50, is slidably disposed inside syringe 20. Plunger 50 preferably comprises an elastomeric cover surface or sealing cover 80 which preferably fits over and is retained upon a forward portion of a plunger assembly 100. One embodiment of plunger assembly 100 is illustrated in FIGS. 2A through 2D. Cover 80 forms a sealing connection with the inner wall of syringe 20. Any contact with the injection medium is preferably made only with cover 80, and, therefore, plunger assembly 100 need not be fabricated from a material chemically and/or biochemically compatible with the injection medium. Plunger assembly 100 is preferably fabricated from a relatively structurally strong material such as a nylon or polycarbonate. Cover 80, on the other hand, is preferably fabricated from an elastomeric material that is chemically and biochemically compatible with the injection medium.

As discussed above, piston 40 cooperates with plunger 50 to impart generally reciprocal linear motion thereto. Piston 40 preferably comprises a stem 42 and a piston head 44 formed on a distal end of stem 42. Piston head 44 preferably extends radially outwardly beyond the radial edge of stem 42. In the embodiment illustrated in FIG. 1, piston head 44 comprises two radially-extending, opposing piston flanges 46 and 48.

Figure 2A:
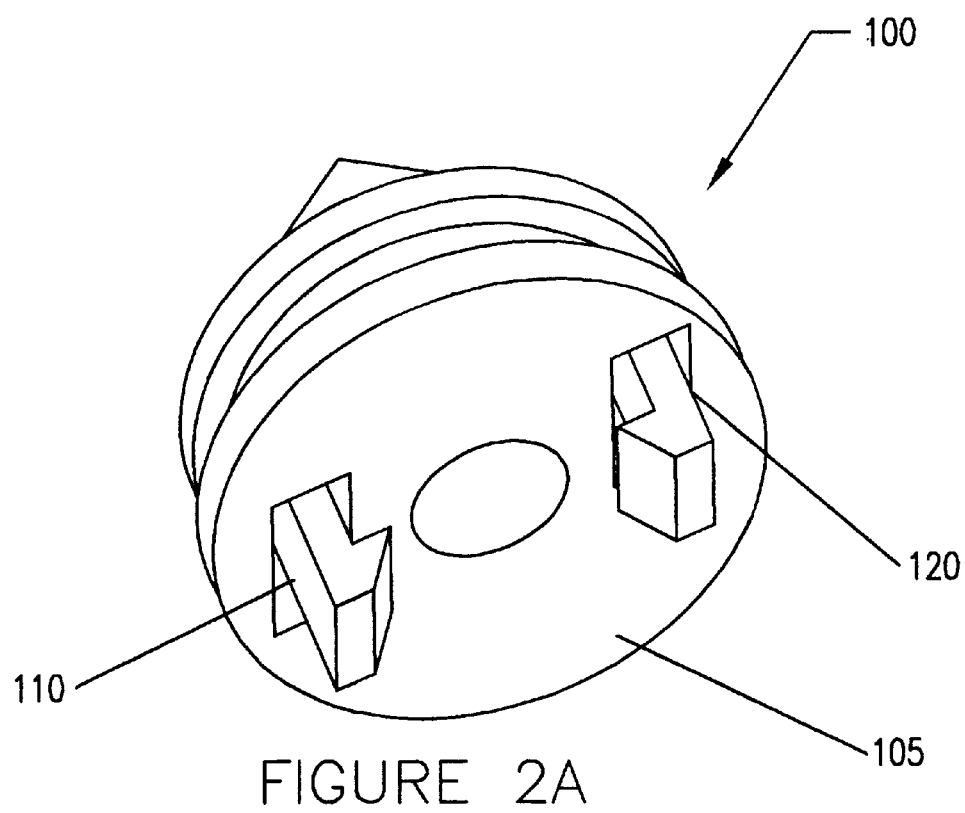
FIG. 2A illustrates a bottom perspective view of an embodiment of a plunger assembly.
Figure 2B:
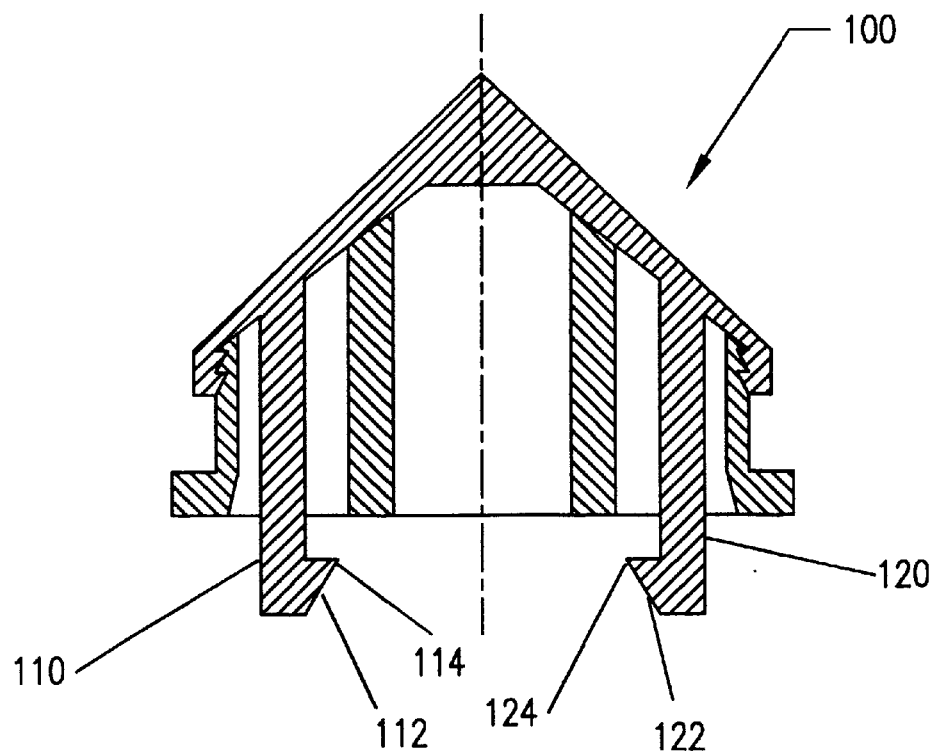
FIG. 2B illustrates a side, cross-sectional view of the plunger assembly of FIG. 2A.
Figure 2C:
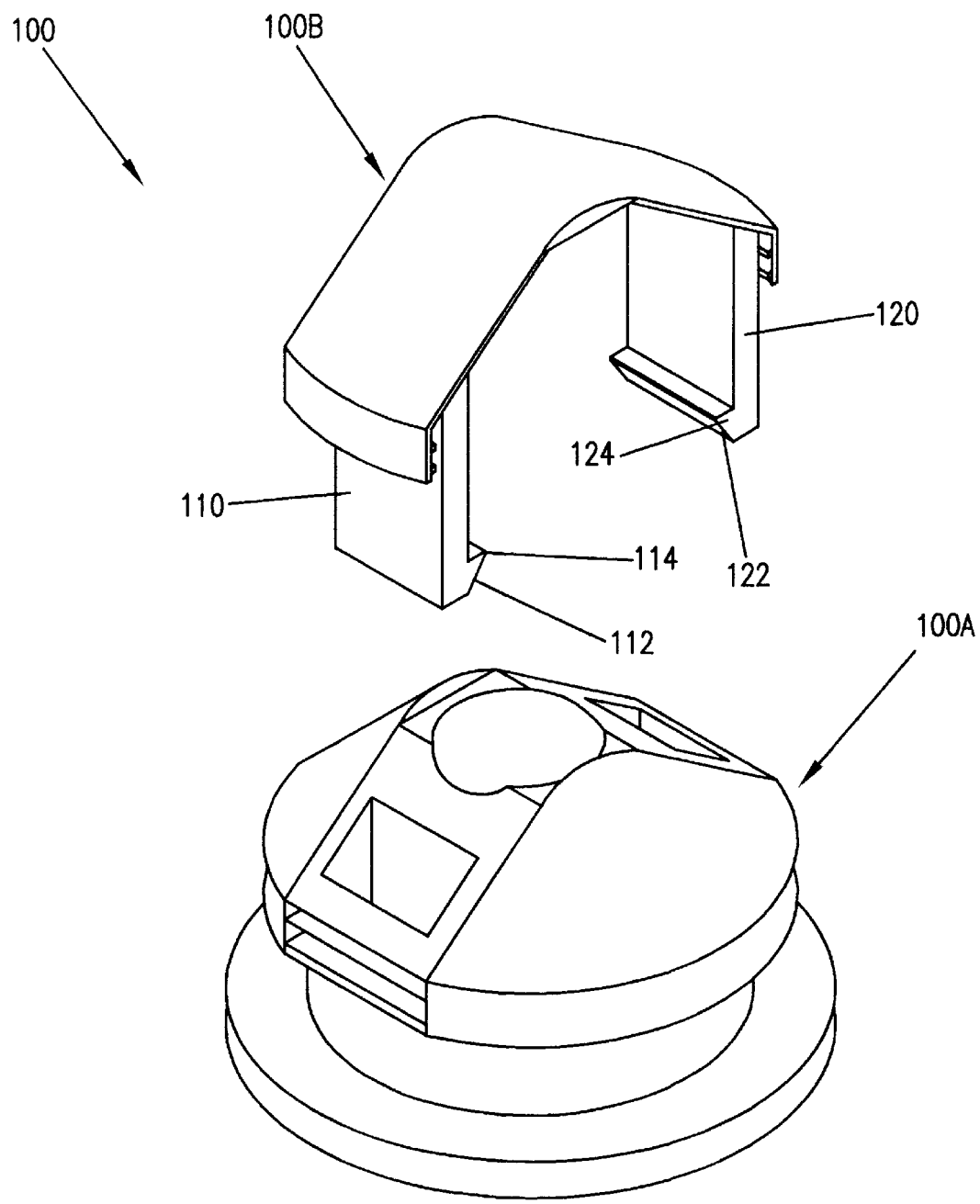
FIG. 2C illustrates a top perspective view of the plunger assembly of FIG. 2A in which the plunger assembly comprises two attachable portions.
Figure 2D:
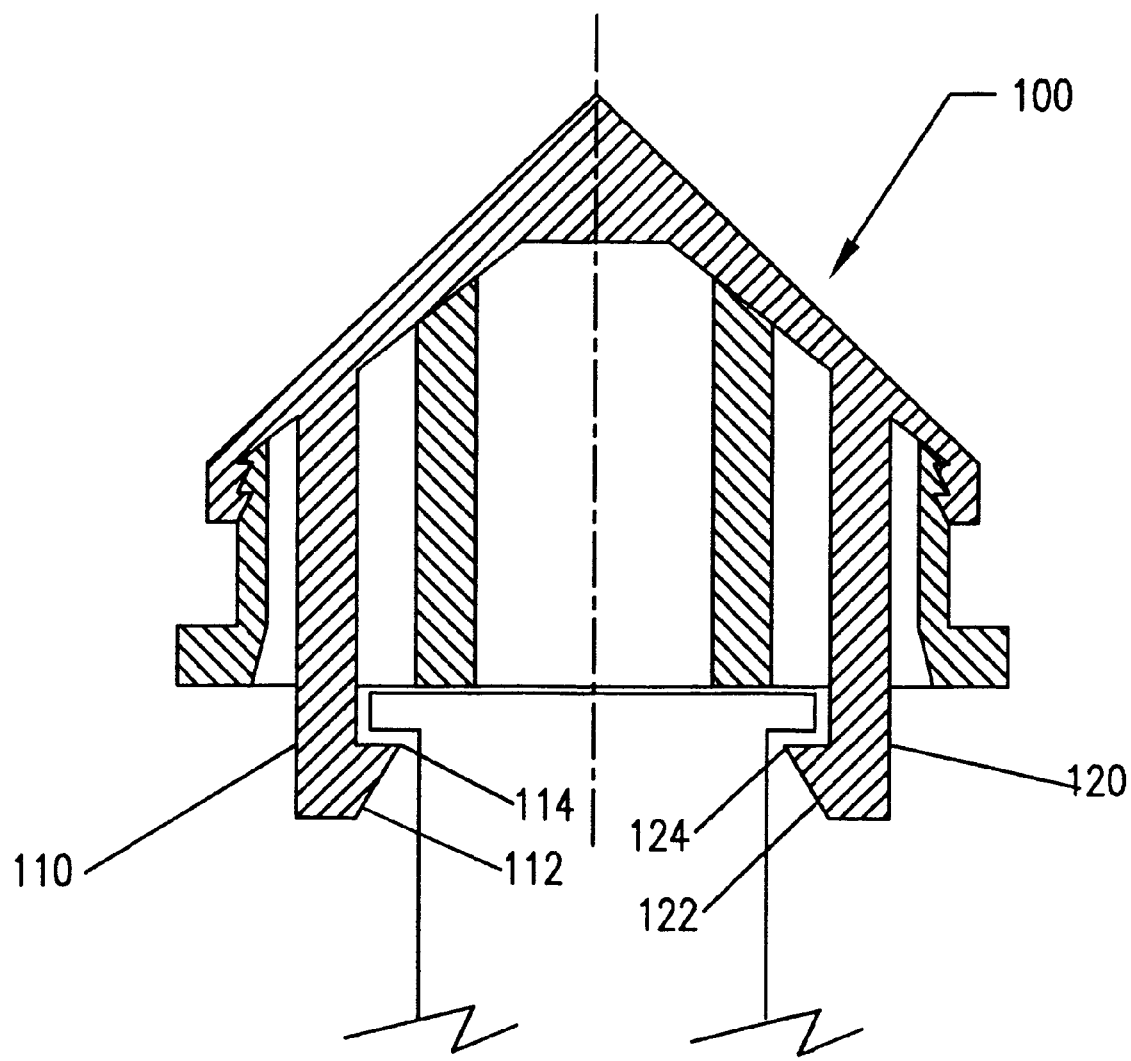
FIG. 2D illustrates a side, cross-sectional view of the plunger assembly of FIG. 2A with a piston connected thereto.

As illustrated in FIGS. 2A through 2D, plunger assembly 100 of plunger 50 preferably includes capture members 110 and 120, which may protrude rearward beyond a rear surface 105 of plunger assembly 100 by an amount sufficient to capture and retain flanges 46 and 48 of the piston head 44 (see, for example, FIG. 2D). In one embodiment, capture members 110 and 120 are preferably constructed of a flexible material such that capture members 110 and 120 flex radially outwardly when contacted by piston flanges 46 and 48 and subsequently "snap back" to capture piston flanges 46 and 48.

In addition, while only two capture members 110 and 120 are shown, as clear to one skilled in the art, more or less than two capture members, for example, one, three or more capture members, may be used with a corresponding change in the shape of the piston head 44.

In a preferred embodiment, as piston 40 moves forward to contact plunger 50 a pair of preferably beveled surfaces 112 and 122 are aligned with and engaged by piston flanges 46 and 48. As a result, capture members 110 and 120 are forced radially outwardly until piston head flanges 46 and 48 pass beyond and over inner shoulders 114 and 124. This design enables piston 40 to engage plunger 50 easily at any axial position of plunger 50.

The user of injector system 5 need only ensure that capture members 110 and 120 are rotated to an engagement position relative to piston flanges 46 and 48 (that is, capture members 110 and 120 are rotated relative to piston flanges 46 and 48 to be in general alignment with piston flanges 46 and 48). The user then may advance piston 40 forward until capture members 110 and 120 contact and capture piston flanges 46 and 48. Preferably, the user is provided with some indication that capture members 110 and 120 have securely engaged piston flanges 46 and 48. This indicator can, for example, simply be the sound that capture members 110 and 120 make when they snap back to capture piston flanges 46 and 48. As clear to one skilled in the art, however, additional indicators (such as indicator lights or position sensors) are easily provided. After engagement, flexible capture members 110 and 120 allow piston head 44 to be rotated about its axis to a disengagement position (wherein capture members 110 and 120 and piston flanges 46 and 48 are no longer in general alignment) for subsequent disengagement and withdrawal of piston 40.

In a preferred embodiment, beveled surfaces 112 and 122 are aligned for engagement with piston flanges 46 and 48 when syringe 20 is properly mounted in retainer 60. Likewise, for the front-loading syringe and injector shown in FIG. 1, disengaging rotation of capture members 110 and 120 relative to piston 40 preferably corresponds to the rotation of syringe 20 required to dismount syringe 20 from retainer 60 so that plunger 50 (which preferably rotates with syringe 20) is disengaged from piston head 44 when syringe 20 is rotated and dismounted from retainer 60.

In an embodiment illustrated in FIGS. 2C and 2D, plunger assembly 100 comprises a first or base member 100A and a second base member or yoke member 100B for ease of fabrication. Plunger assembly 100 can, however, be fabricated to be integral or single-piece.

Figure 3A:
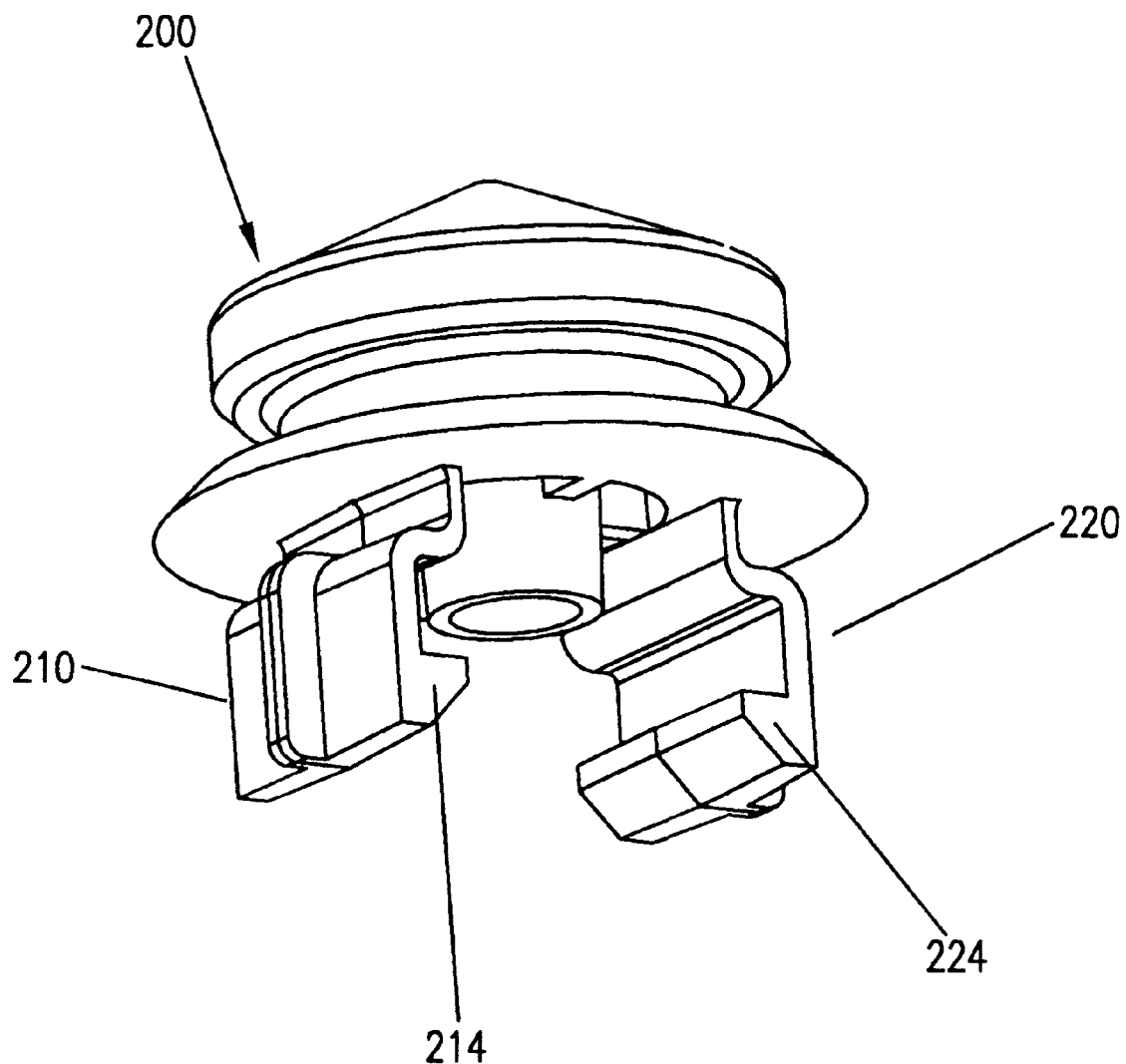
FIG. 3A illustrates a bottom perspective view of an embodiment of a single-piece plunger comprising capture members providing resistance to disconnection of the plunger and the piston upon rearward motion of the piston.
Figure 3B:
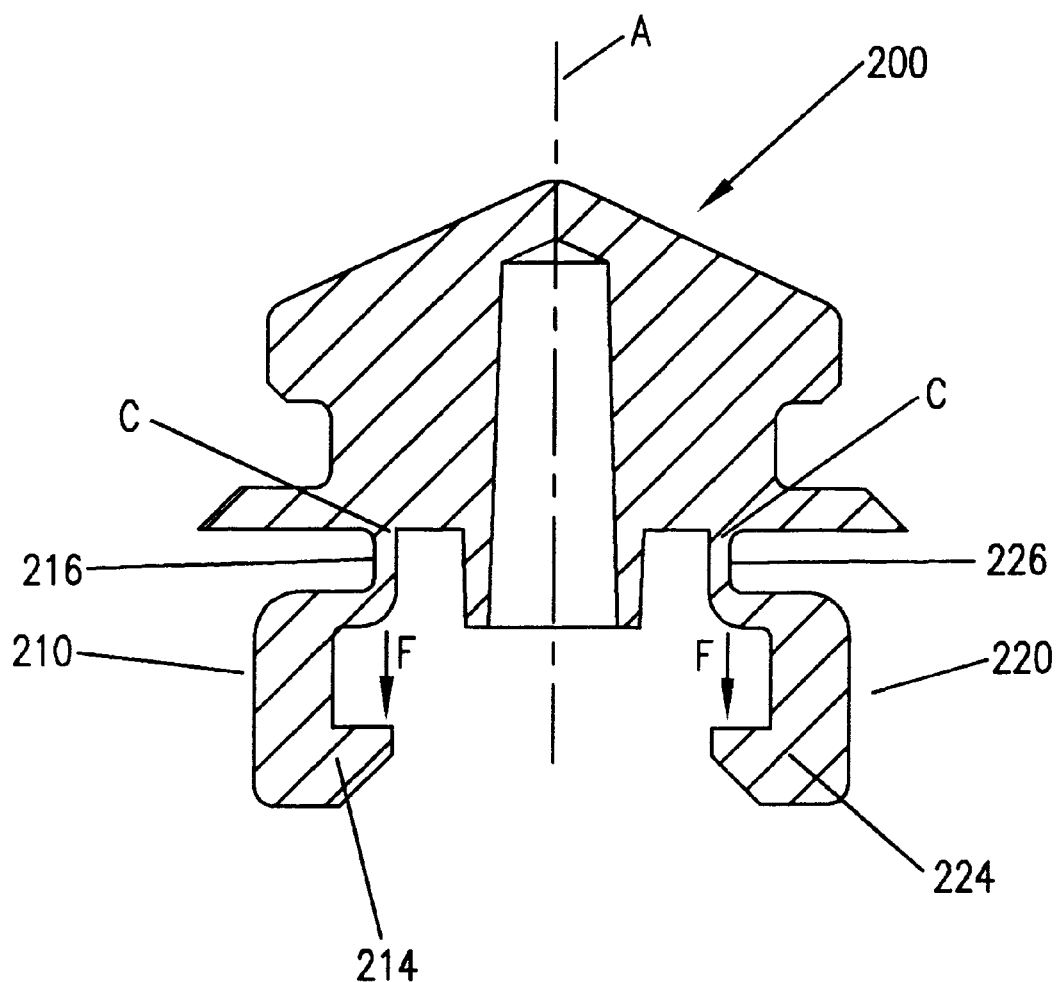
FIG. 3B illustrates a side, cross-sectional view of the single-piece plunger of FIG. 3A.

After retention of piston head 44, plunger 50 preferably resists disconnection from piston 40 upon rearward movement of piston 40 unless plunger 50 has been rotated relative to piston head 44 to a disengagement position. In the embodiment illustrated in FIGS. 3A through 3B, for example, plunger assembly 200 comprises capture members 210 and 220 that are designed such that the forces exerted upon capture members 210 and 220 upon rearward movement of piston 40 substantially prevent radially outward deflection (or bending) of capture members 210 and 220. As illustrated in FIG. 3B, shoulders or retention members 214 and 224 of capture members 210 and 220 are preferably positioned (or cantilevered) about axis A such that the load experienced upon rearward movement of piston 40 (represented by arrows F) is experienced at a position equal or greater in radial distance (relative to axis A) than points C where stems 216 and 226 of cantilevered capture members 210 and 220 are anchored or attached to base 200. The bending moment created by rearward motion of piston 40 thus tends to cause capture members 210 and 220 to deflect (if at all) radially inwardly and assists in preventing disconnection of plunger 50 from piston 40.

Figure 4A:
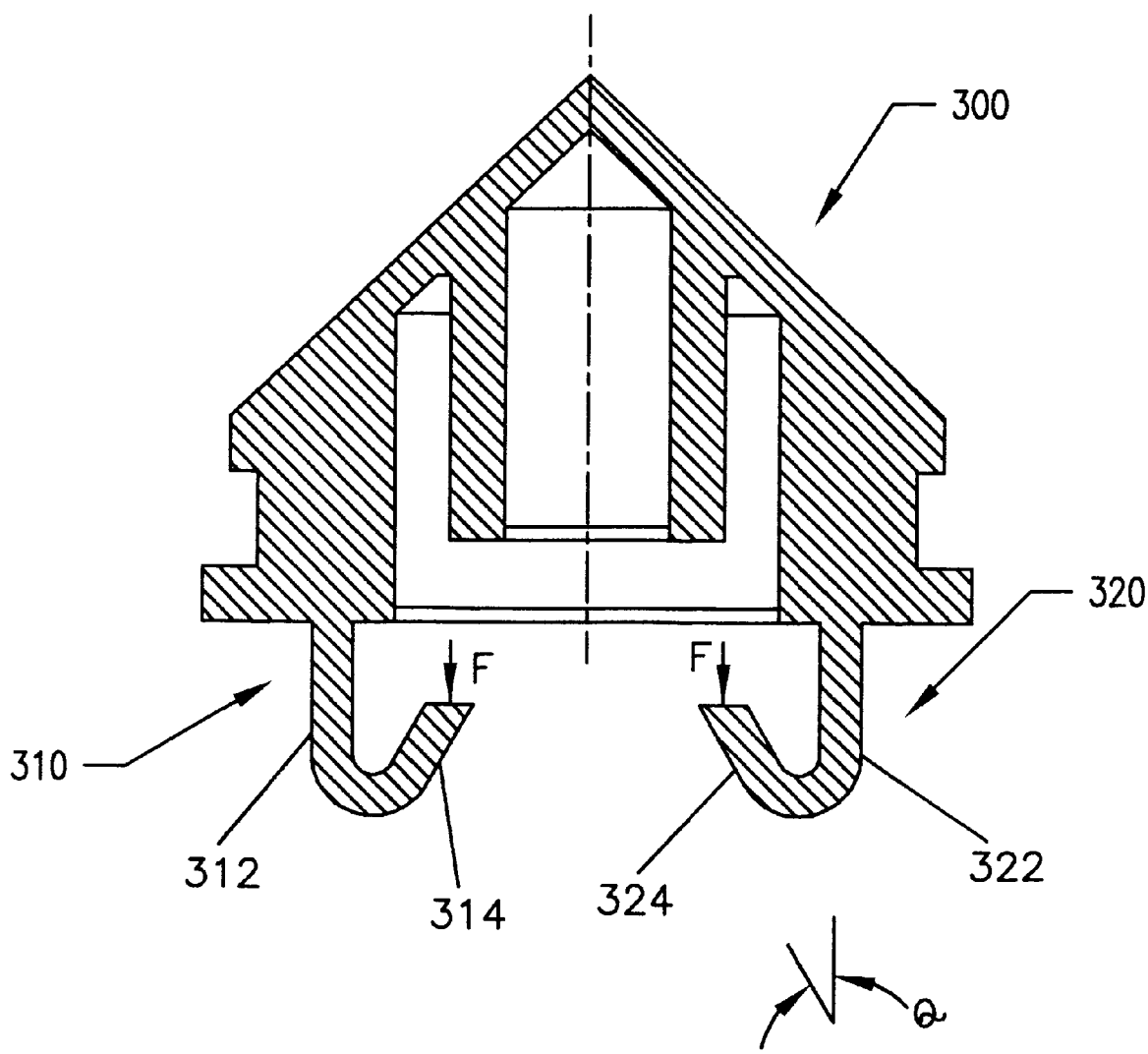
FIG. 4A illustrates a side, cross-sectional view of an embodiment of a single-piece plunger comprising V-shaped capture members to capture and retain the piston.
Figure 4B:
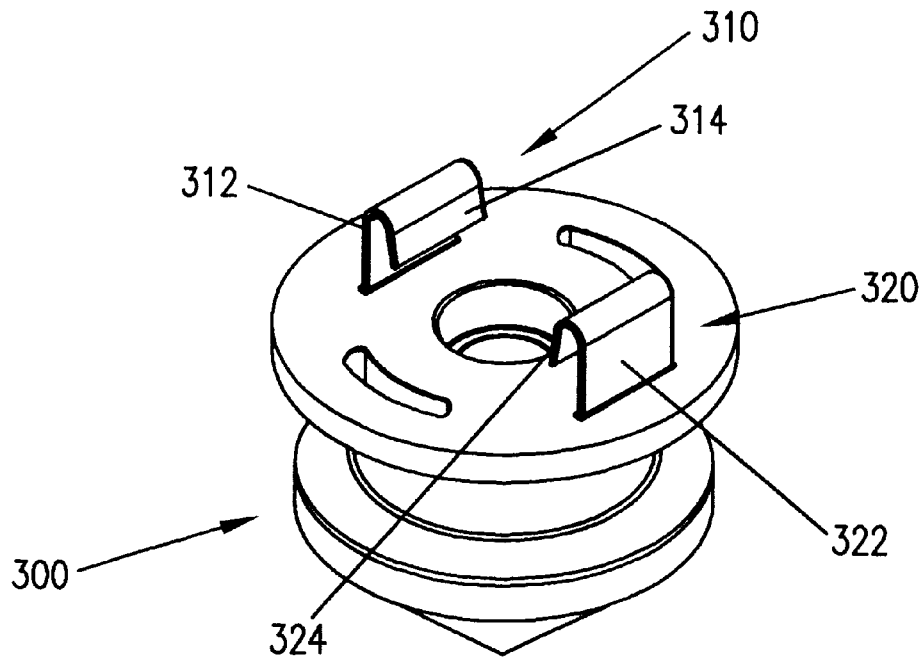
FIG. 4B illustrates a bottom perspective view of the single-piece plunger of FIG. 4A.
Figure 4C:
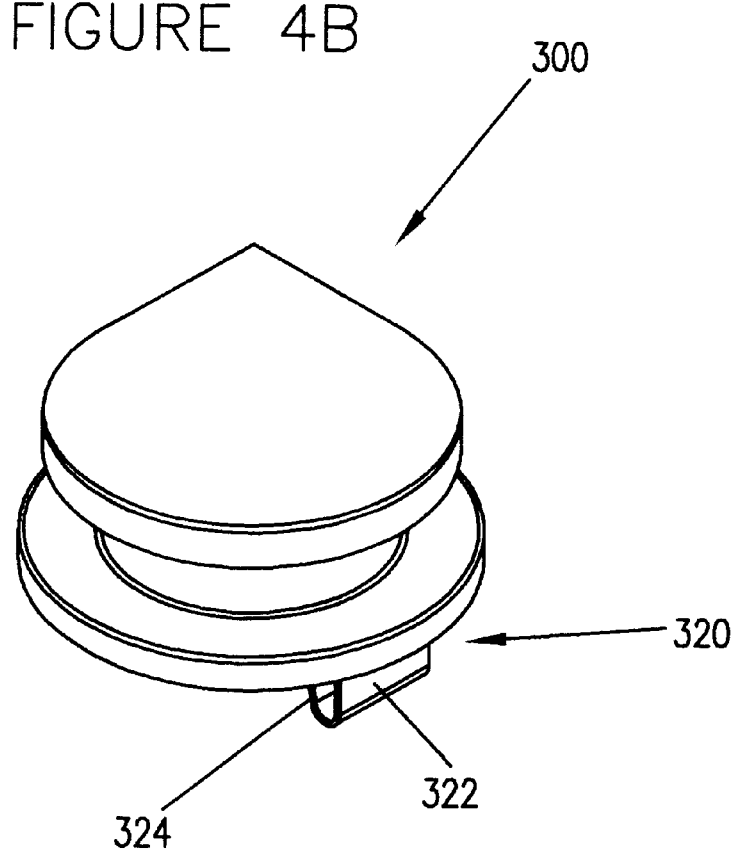
FIG. 4C illustrates a top perspective view of the single-piece plunger of FIG. 4A.

In another embodiment illustrated in FIGS. 4A through 4C, assembly 300 preferably comprises generally V-shaped capture members 310 and 320. In that regard, capture members 310 and 320 comprise support members 312 and 322, respectively, which preferably extend rearward from plunger assembly 300. Capture members 310 and 320 also comprise retention members 314 and 324, respectively, that extend radially inward (that is, towards axis A) and forward (that is, toward plunger assembly 300) from support members 312 and 322, respectively, at an angle θ.

Upon linear forward motion of piston 40, piston flanges 46 and 48 contact retention members 314 and 324 and cause retention members 314 and 324 to flex radially outwardly to allow piston head 44 to pass beyond retention members 314 and 324. Once piston flanges 46 and 48 pass by the forward ends of retention members 314 and 324, retention members 314 and 324 return to substantially their unflexed position to retain piston head 44. Retention members 314 and 324 resist disconnection of plunger assembly 300 and piston 40 upon rearward motion of piston 40. Force F, arising from rearward motion of piston 40, results in flexing of retention members 314 and 324 away from base 300 (that is, an increase in angle θ). This result tends to keep retention members 314 and 324 in contact with piston flanges 46 and 48 and to prevent disengagement of capture members 310 and 320 from piston 40 upon rearward motion of piston 40.

As discussed in connection with each of the above embodiments, the capture members may be fabricated such that at least a portion thereof flexes or springs radially outwardly to allow flanges 46 and 48 to pass. Alternatively, the capture members of the above embodiments can be fabricated to be substantially rigid and piston flanges 46 and 48 can be fabricated to be flexible or spring-loaded such that piston flanges 46 and 48 deflect radially inwardly (with respect to axis A) to allow passage of piston head 44 between the capture members and subsequent retention of piston head 44 by the capture members once piston flanges 46 and 48 "spring back" to their original position.

Figure 5A:
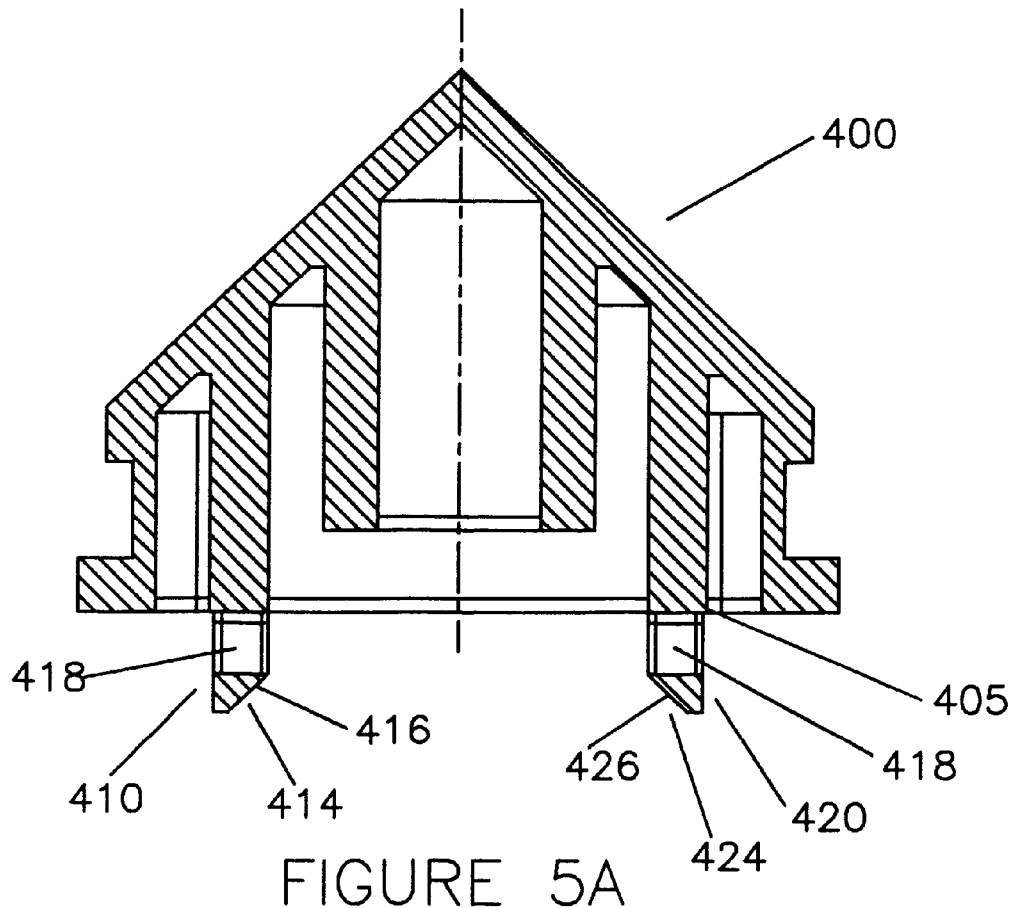
FIG. 5A illustrates a side, cross-sectional view of an embodiment of a single-piece plunger comprising capture members adapted to engage and retain radially movable piston flanges.
Figure 5B:
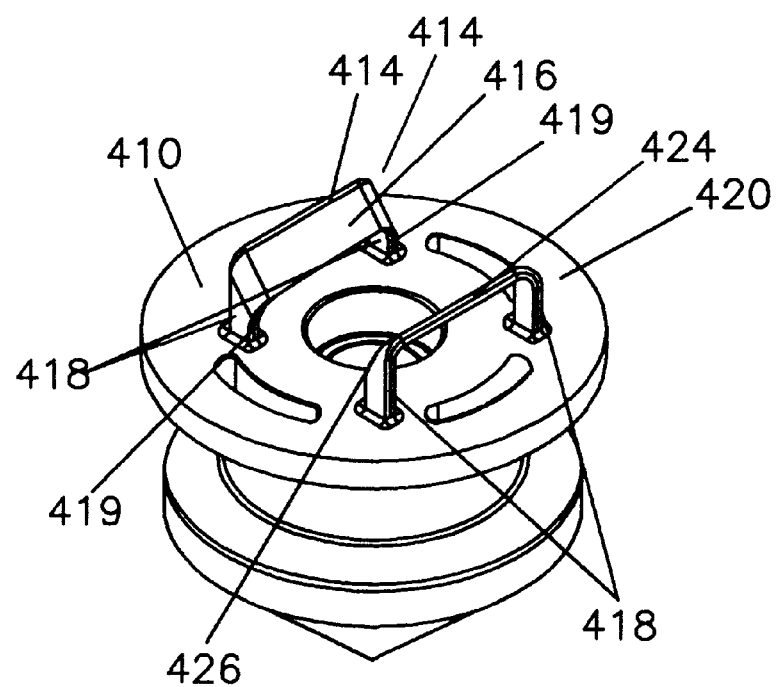
FIG. 5B illustrates a bottom perspective view of the single-piece plunger of FIG. 5A.

FIGS. 5A and 5B illustrate another embodiment of a plunger assembly 400 preferably adapted to retain piston flanges 46 and 48 which deflect radially inwardly upon contacting capture members 410 and 420. Piston flanges 46 and 48, for example, can be flexible or spring-load to deflect radially inward upon contact with capture members 410 and 420 and subsequently return to their original position to be retained by capture members 410 and 420. In that regard, capture members 410 and 420 preferably comprise retention members 414 and 424, respectively. Retention members 414 and 424 preferably comprise beveled surfaces 416 and 426, respectively, to facilitate radially inward deflection of piston flanges 46 and 48 upon contact therewith. Capture members 410 and 420 further preferably comprise support members 418. Support members 418 are preferably attached to the distal ends of retention members 414 and 424 as well as to rear surface 405 of plunger assembly 400. After piston flanges 46 and 48 pass by the forwardmost edge of beveled surfaces 416 and 426, piston flanges 46 and 48 are free to spring radially outward to be retained by U-shaped retention members 410 and 420. Retention members 414 and 424 prevent disconnection of piston 40 from plunger 50 upon rearward motion of piston 40.

Piston 40 can be disengaged or disconnected from retention by capture members 410 and 420 by rotation of plunger 50 (and thereby plunger assembly 400) relative to piston 40. In that regard, the edges of piston flanges 46 and 48 are preferably rounded to facilitate radially inward deflection of piston flanges 46 and 48 upon contact with support members 418 when plunger 50 is rotated relative to piston 40. Likewise, support members 418 preferably comprise beveled surfaces 419 to further facilitate radially deflection of piston flanges 46 and 48.

Figure 6A:
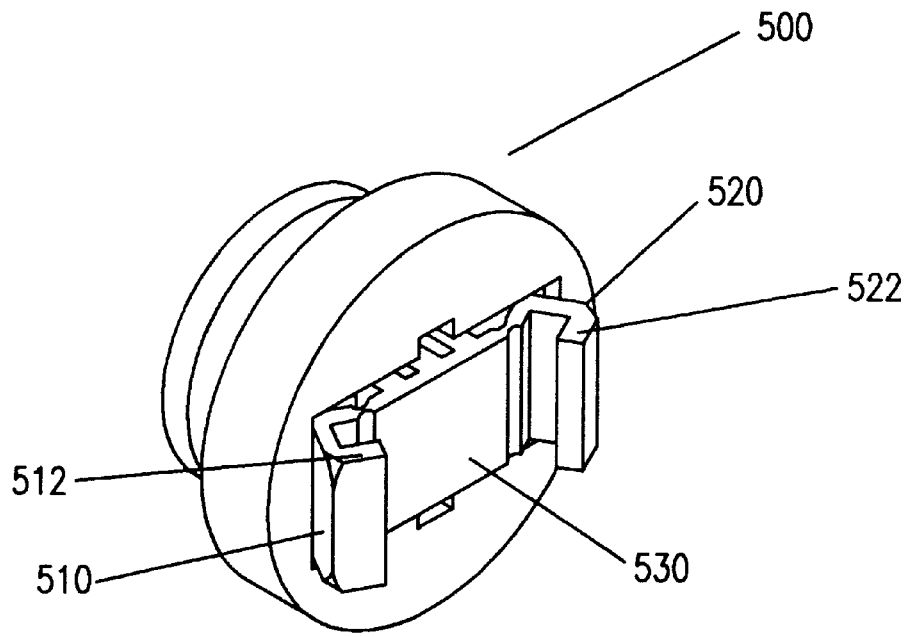
FIG. 6A illustrates a bottom perspective view of an embodiment of a plunger assembly in which the capture members are moveably hinged to capture and retain a piston.

In still a further embodiment, plunger assembly 500 comprises rotatably or pivotally moveable capture members 510 and 520. In the embodiment illustrated in FIGS. 6A through 6C, capture members 510 and 520 are preferably initially hinged radially outwardly (see FIG. 6A) a sufficient amount to allow piston flanges 46 and 48 to pass by retention shoulders 512 and 522 of capture members 510 and 520, respectively, without contacting retention shoulders 512 and 522. When piston head 44 contacts surface 530, capture members 510 and 520 are caused to rotate or hinge radially inward to capture and retain piston flanges 46 and 48.

Figure 6B:
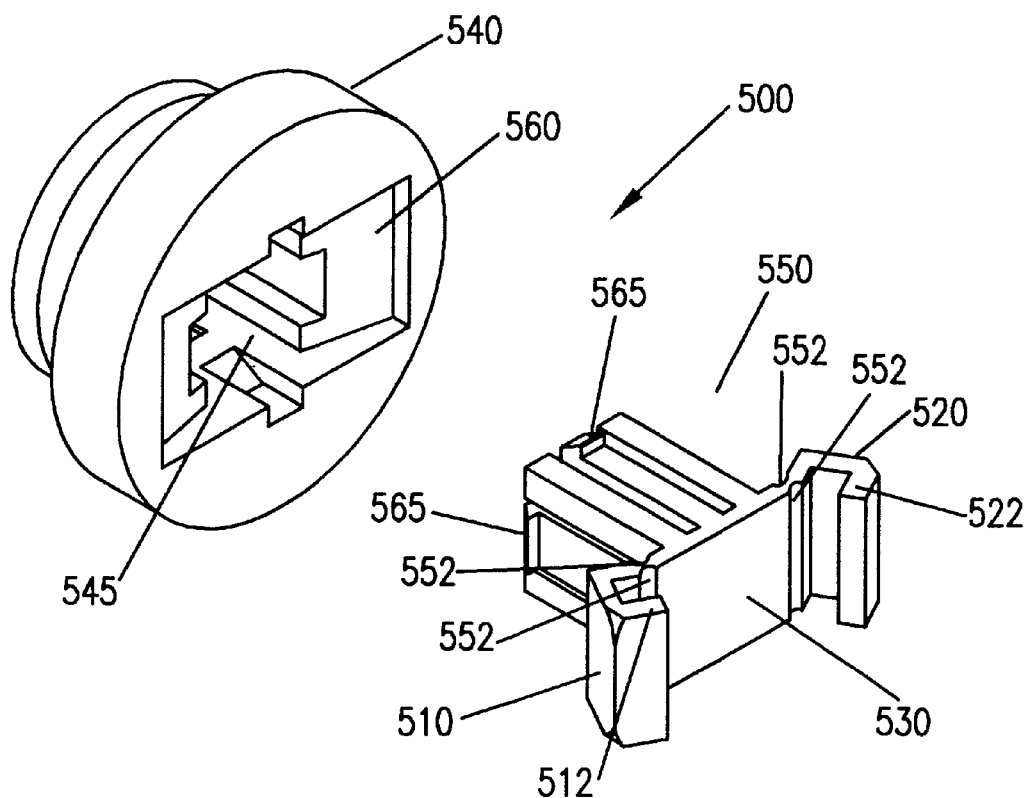
FIG. 6B illustrates a bottom perspective view of an embodiment of the plunger assembly of FIG. 6A comprising two attachable portions.

As best illustrated in FIG. 6B, plunger assembly 500 is preferably fabricated in two portions 540 and 550. Second portion 550, which comprises capture members 510 and 520, is preferably fabricated from a resilient polymeric material. Second portion 550 preferably comprises "plastic hinges" formed by creating notches 552 in second portion 550. These plastic hinges or thinned areas allow capture members 510 and 520 to hinge or rotate about the general center of notches 552.

Figure 6C:
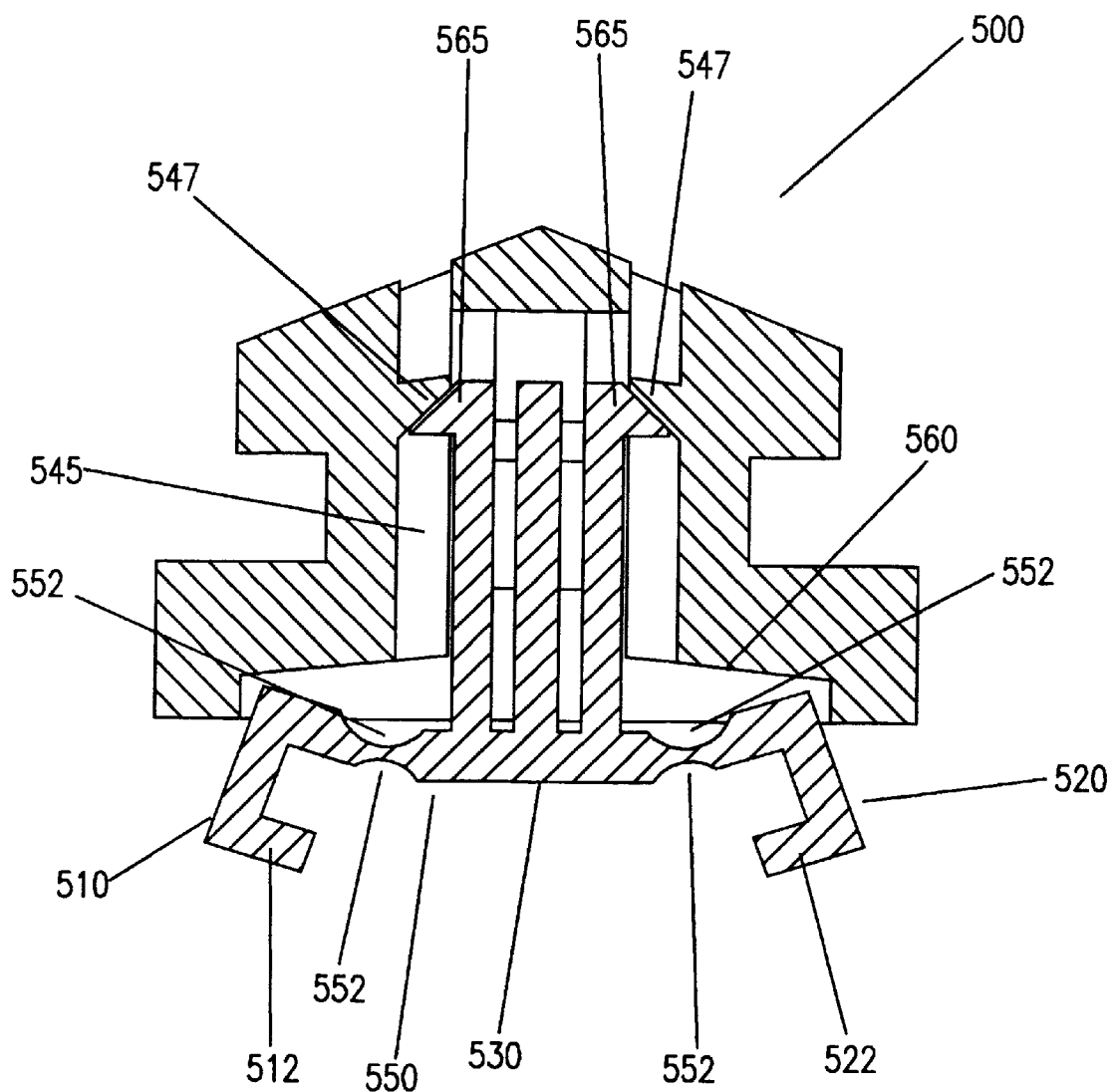
FIG. 6C illustrates a side, cross-sectional view of the plunger assembly of FIG. 6B.

As best understood from FIG. 6B and 6C, upon contact of piston head 44 with contact surface 530, second portion 550 moves forward via passage 545 so that capture members 510 and 520 contact surface 560 and are forced to rotate or hinge radially inwardly to capture and retain piston flanges 46 and 48. Second portion 550 preferably comprises at least one attachment member to secure second portion in a forward position after capture members 510 and 520 rotate inwardly to capture piston flanges 46 and 48. For example, second portion preferably comprises flexible attachment members 565 which cooperate with abutment members 547 to secure second portion 550 in a forward position. Because second portion is secured in a forward position, capture members 510 and 520 resist radially outward rotation thereof during rearward motion of piston 40 and thereby resist disconnection from piston head 44 upon rearward motion of piston 40. Piston 40 can be disengaged from capture members 510 and 520, however, by rotation of plunger 50 relative to piston 40.

Figure 7E:
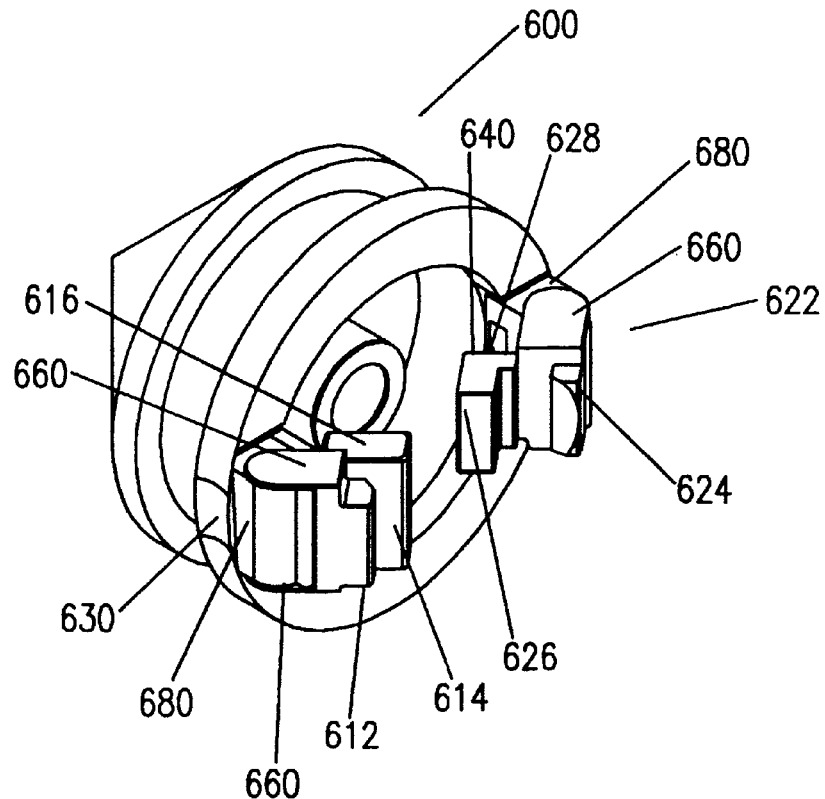
FIG. 7E illustrates a bottom perspective view of the plunger assembly of FIG. 7A.
Figure 7C:
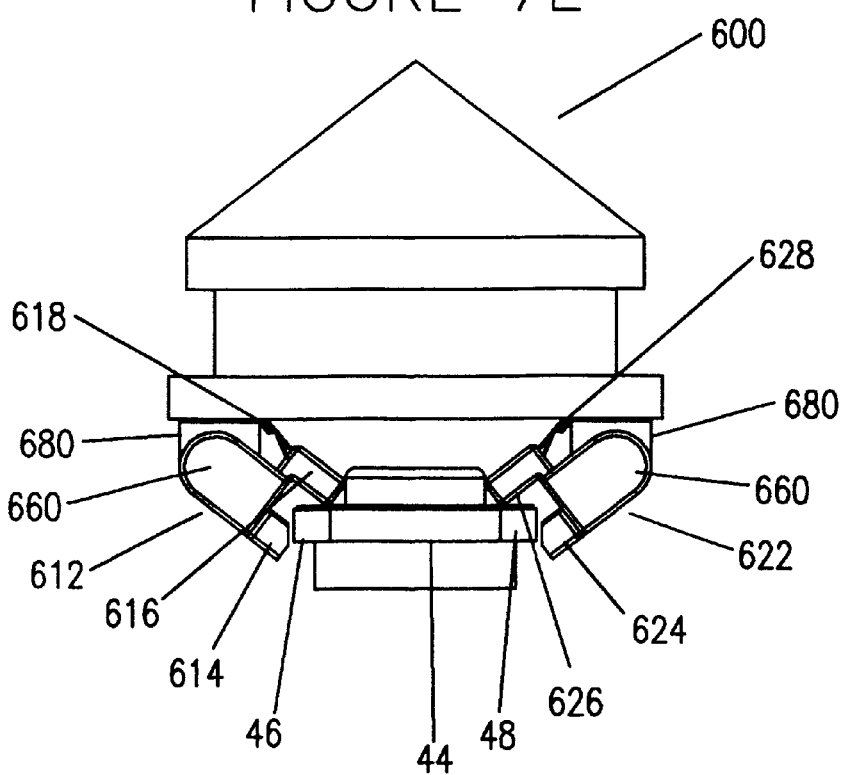
FIG. 7C illustrates a side view of the plunger assembly of FIG. 7A in which the piston is shown in its initial contact position with the capture members.

In an alternative embodiment illustrated in FIGS. 7A through 7E, plunger assembly 600 comprises capture members 610 and 620, which include rotatable retention members 612 and 622. As illustrated in FIGS. 7B and 7E, retention shoulders 614 and 624 of retention members 612 and 622, respectively, are initially rotated radially outward such that piston flanges 46 and 48 can pass retention shoulders 614 and 624 without contact therewith. During forward motion of piston 40, piston flanges 46 and 48 contact rear shoulders 616 and 626 of retention members 612 and 622, respectively, thereby causing retention shoulders 614 and 624 to rotate inwardly to capture and retain piston flanges 46 and 48 (see FIG. 7A).

Retention members 612 and 622 preferably comprise protruding attachment members 618 and 628 which cooperate with cooperating retainers 630 and 640 formed in plunger assembly 600 to substantially prevent rotation of retention members 612 and 622 once piston head 44 is engaged and retained. Piston 40 can be disengaged from capture members 610 and 620 by rotation of plunger 50 relative to piston 40 and subsequent rearward movement of piston 40.

As illustrated in FIG. 7D, capture members 610 and 620 are preferably fabricated such that rotatable retention members 612 and 622 are formed separately from the remainder of plunger assembly 600. Retention members 612 and 622 comprise protrusions 650 formed on resilient extending members 660. Protrusions 650 cooperate with circular recesses 670 formed on support members 680 to allow retention members 612 and 622 to rotate around axis A' and axis A", respectively.

The embodiments illustrated in FIGS. 6A through 7C not only create a firm (yet releasable) connection of plunger 50 and piston 40, but are also suitable to prevent easy reuse of a syringe. Such reuse is typically undesirable, for example, to reduce the risk of cross contamination between patients. In the embodiments illustrated in FIGS. 6A through 7C, plunger 50 comprises a mechanism that substantially prevents reconnection (that is, prevents reconnection without substantial effort from the user) of piston 40 to plunger 50 after an initial connection therebetween.

The present invention has been described above in terms of releasable mechanisms attached to or formed on syringe plungers. It is specifically contemplated, however, that the releasable connection mechanisms of the present invention may be incorporated on the drive members or pistons of injectors.

Furthermore, the present invention has been described above generally in terms of two or more capture or other structural members for releasably engaging an injector drive member. It is specifically contemplated that a single capture member, as well as three or more capture members, may be used to form releasable connection mechanisms.

The embodiments of the invention described above are to be considered in all respects only as illustrative and not restrictive. The scope of the invention is indicated by the following claims rather than by the foregoing description. All changes which come within the meaning and range of equivalency of the claims are to be embraced within their scope.

What is claimed is:

1. A plunger adapted to be releasably connected to an injector drive member by means of a releasable connection mechanism, the releasable connection mechanism comprising at least one capture member associated with one of the plunger and the drive member, the at least one capture member adapted to form a releasable engagement with the other of the drive member and the plunger upon contact of the drive member with the plunger during linear forward motion of the drive member relative to the plunger when the at least one capture member is in an engagement position, the at least one capture member further being adapted to release one of the drive member and the plunger upon relative rotation of the at least one capture member to a disengagement position.

2. The plunger of claim 1 wherein the at least one capture member comprises two capture members.

3. The plunger of claim 1 wherein the at least one capture member is associated with the plunger.

4. The plunger of claim 1 wherein the at least one capture member is fabricated from a relatively flexible material and deflects radially outwardly upon contact with the other of the drive member and the plunger.

5. The plunger of claim 4, further comprising at least one radially outward extending flange associated with the other of the drive member and the plunger, the at least one flange cooperable with the at least one capture member to releasably connect the drive member and the plunger.

6. The plunger of claim 1 wherein the at least one capture member is fabricated from a relatively rigid material and deflects radially inwardly upon contact with the other of the drive member and the plunger.

7. The plunger of claim 3 wherein the at least one capture member is adapted to resist disengagement from the drive member when the drive member is moved rearward and the drive member and the at least one capture member are connected in the engagement position.

8. The plunger of claim 3 wherein the at least one capture member comprises rotatable retention members, the retention members comprising a retention shoulder that rotates to retain the drive member in contact with the retention members when the drive member and the at least one capture member are in the engagement position.

9. The plunger of claim 1, further comprising a mechanism that substantially prevents reconnection of the drive member to the plunger after an initial connection therebetween has been disconnected.

10. A syringe comprising:

a main body portion;

a plunger slidably disposed within the main body portion, the plunger adapted to be releasably connected to an injector drive member; and a releasable connection mechanism adapted to make a releasable connection between the plunger and the injector drive member, the releasable connection mechanism comprising at least one capture member attached to one of the plunger and the drive member, the at least one capture member adapted to form a releasable engagement with the other of the drive member and the plunger upon contact of the drive member with the plunger during linear forward motion of the drive member relative to the plunger when the at least one capture member is in an engagement position, the at least one capture member further being adapted to resist disengagement from one of the drive member and the plunger when the drive member is moved rearward and the at least one capture member is in an engagement position and to release one of the drive member and the plunger upon relative rotation of the at least one capture member to a disengagement position.

11. The syringe of claim 10 wherein the at least one capture member comprises at least two capture members.

12. An injector system for injecting a fluid medium, the injector system comprising:

an injector comprising a drive member, the drive member being movable in a generally reciprocal linear manner;

a syringe comprising a main body portion and a plunger slidably disposed within the main body portion; and a releasable connection mechanism operable to releasably connect the drive member and the plunger, the connection mechanism comprising at least two capture members attached to the plunger, the capture members adapted to form a releasable connection upon contact of the drive member with the capture members during linear forward motion of the drive member relative to the plunger when the capture members are in an engagement position relative to the drive member, the capture members further being adapted to release the drive member upon relative rotation of the capture members to a disengagement position relative to the drive member.

13. A syringe for use with an injector having a drive member, the syringe comprising:

a body portion; and a plunger slidably disposed within the body portion, the plunger comprising a releasable connection mechanism adapted to make a releasable connection with a connection member on the injector drive member, the releasable connection mechanism comprising at least one capture member attached to the plunger, the at least one capture member adapted to form a releasable engagement with the connection member upon contact of the drive member with the at least one capture member during forward motion of the drive member relative to the plunger when the at least one capture member is in an engagement position relative to the drive member, the at least one capture member further being adapted to resist disengagement from the connection member of the drive member when the drive member is moved rearward and the drive member and the at least one capture member are in the engagement position and to release the drive member upon rotation of the at least one capture member to a disengagement position relative to the drive member.

14. A syringe plunger adapted to be releasably connected to a drive member of an injector by means of a releasable connection mechanism, the releasable connection mechanism comprising at least one capture member associated with one of the plunger and the drive member, the at least one capture member adapted to form a releasable connection with the other of the drive member and the plunger upon contact of the drive member with the plunger during forward motion of the drive member relative to the plunger when the at least one capture member is in an engagement position, the at least one capture member further being adapted to resist disengagement from the other of the drive member and the plunger when the drive member is moved rearward and the at least one capture member is in the engagement position and to release one of the drive member and the plunger upon rotation of the at least one capture member to a disengagement position.

15. A plunger adapted to be releasably connected to an injector drive member by means of a releasable connection mechanism, the releasable connection mechanism comprising at least one capture member associated with one of the plunger and the drive member, the at least one capture member being fabricated from a relatively flexible material and adapted to deflect radially outwardly to cooperably form a releasable engagement with at least one radially outward extending flange associated with the other of the drive member and the plunger upon contact of the drive member with the plunger during linear forward motion of the drive member relative to the plunger when the at least one capture member is in an engagement position.

16. A plunger adapted to be releasably connected to an injector drive member by means of a releasable connection mechanism, the releasable connection mechanism comprising at least one capture member associated with the plunger, the at least one capture member adapted to form a releasable engagement with the drive member upon contact of the drive member with the plunger during linear forward motion of the drive member relative to the plunger when the at least one capture member is in an engagement position, the at least one capture member further being adapted to resist disengagement from the drive member when the drive member is moved rearward and the drive member and the at least one capture member are connected in the engagement position.

17. The syringe of claim 10 wherein the at least one capture member is associated with the plunger.

18. The syringe of claim 10 wherein the at least one capture member deflects radially outwardly upon contact with the other of the drive member and the plunger.

19. The syringe of claim 18, further comprising at least one radially outward extending flange associated with the other of the drive member and the plunger, the at least one flange cooperable with the at least one capture member to releasably connect the drive member and the plunger.

20. The syringe of claim 10 wherein the at least one capture member deflects radially inwardly upon contact with the other of the drive member and the plunger.

21. The syringe of claim 17 wherein the at least one capture member comprises rotatable retention members, the retention members comprising a retention shoulder that rotates to retain the drive member in contact with the retention members when the drive member and the at least one capture member are in the engagement position.

22. The syringe of claim 10, further comprising a mechanism that substantially prevents reconnection of the drive member to the plunger after an initial connection therebetween has been disconnected.

23. The injector system of claim 12 wherein the at least one capture member deflects radially outwardly upon contact with the drive member.

24. The injector system of claim 23, further comprising at least one radially outward extending flange associated with the drive member, the at least one flange cooperable with the at least one capture member to releasably connect the drive member and the plunger.

25. The injector system of claim 12 wherein the at least one capture member deflects radially inwardly upon contact with the drive member.

26. The injector system of claim 12 wherein the at least one capture member is adapted to resist disengagement from the drive member when the drive member is moved rearward and the drive member and the at least one capture member are connected in the engagement position.

27. The injector system of claim 12 wherein the at least one capture member comprises rotatable retention members, the retention members comprising a retention shoulder that rotates to retain the drive member in contact with the retention members when the drive member and the at least one capture member are in the engagement position.

28. The injector system of claim 12, further comprising a mechanism that substantially prevents reconnection of the drive member to the plunger after an initial connection therebetween has been disconnected.

29. The syringe of claim 13 wherein the at least one capture member comprises two capture members.

30. The syringe of claim 13 wherein the at least one capture member deflects radially outwardly upon contact with the drive member.

31. The syringe of claim 30, further comprising at least one radially outward extending flange associated with the drive member, the at least one flange cooperable with the at least one capture member to releasably connect the drive member and the plunger.

32. The syringe of claim 13 wherein the at least one capture member deflects radially inwardly upon contact with the drive member.

33. The syringe of claim 13 wherein the at least one capture member comprises rotatable retention members, the retention members comprising a retention shoulder that rotates to retain the drive member in contact with the retention members when the drive member and the at least one capture member are in the engagement position.

34. The syringe of claim 13, further comprising a mechanism that substantially prevents reconnection of the drive member to the plunger after an initial connection therebetween has been disconnected.

35. The syringe plunger of claim 14 wherein the at least one capture member is associated with the plunger.

36. The syringe plunger of claim 14 wherein the at least one capture member comprises two capture members.

37. The syringe plunger of claim 14 wherein the at least one capture member deflects radially outwardly upon contact with the other of the drive member and the plunger.

38. The syringe plunger of claim 37, further comprising at least one radially outward extending flange associated with the other of the drive member and the plunger, the at least one flange cooperable with the at least one capture member to releasably connect the drive member and the plunger.

39. The syringe plunger of claim 14 wherein the at least one capture member deflects radially inwardly upon contact with the other of the drive member and the plunger.

40. The syringe plunger of claim 35 wherein the at least one capture member comprises rotatable retention members, the retention members comprising a retention shoulder that rotates to retain the drive member in contact with the retention members when the drive member and the at least one capture member are in the engagement position.

41. The syringe plunger of claim 14, further comprising a mechanism that substantially prevents reconnection of the drive member to the plunger after an initial connection therebetween has been disconnected.

* * * * *

UNITED STATES PATENT AND TRADEMARK OFFICE
Certificate

Patent No. 5,947,935                                                                                       Patented: September 7, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Daniel Kazousky; Michael C. Andreen; Edward J. Rhinehart; David M. Reilly; Mark W. Hitchins; Anthony S. McCoppin Signed and Sealed this Twenty-Fourth Day of April, 2001.

<div style="text-align:right">

RICHARD SEIDEL
*Supervisory Patent Examiner*
Art Unit 3763

</div>